Figure 1:
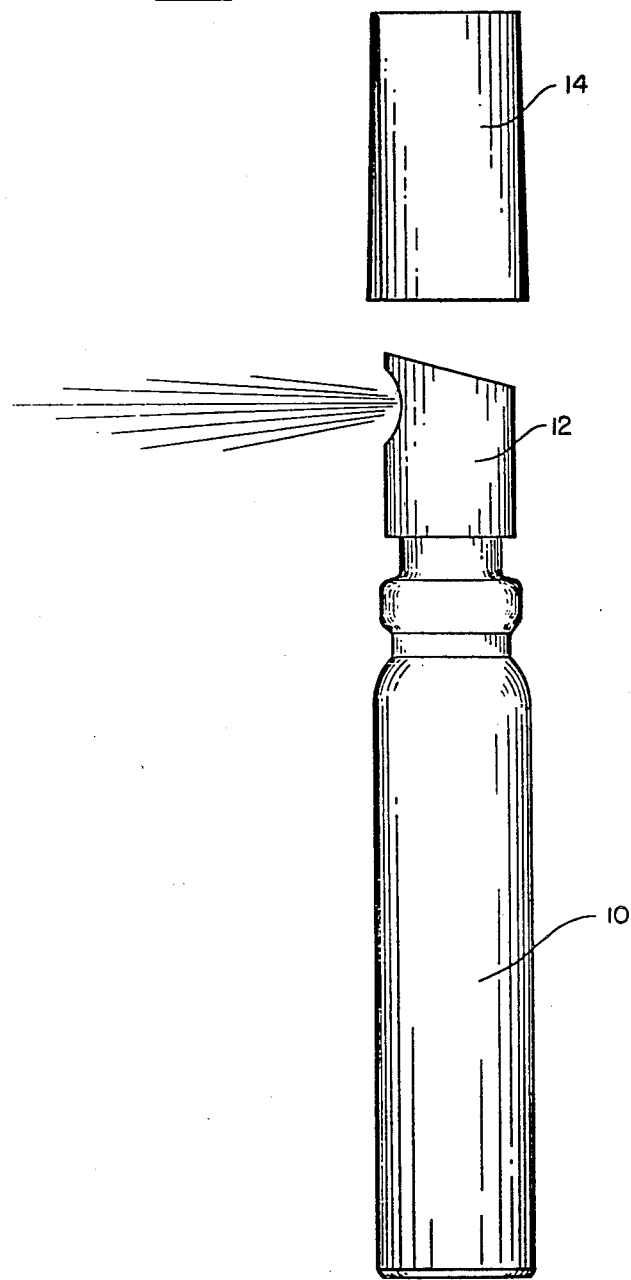

United States Patent [19]

Jacobs

[11] Patent Number: 4,635,651
[45] Date of Patent: Jan. 13, 1987

[54] PROCESS FOR THE INCLUSION OF A SOLID PARTICULATE COMPONENT INTO AEROSOL FORMULATIONS OF INHALABLE NICOTINE

[76] Inventor: Allen W. Jacobs, 12534 Oxnard St., #6, North Hollywood, Calif. 91606

[21] Appl. No.: 182,639

[22] Filed: Aug. 29, 1980

[51] Int. Cl.$^4$ ............................................. A24F 47/00
[52] U.S. Cl. ..................................... 131/270; 131/271; 131/329
[58] Field of Search ....................... 131/270, 271, 329; 128/200.14

[56] References Cited

U.S. PATENT DOCUMENTS 3,679,102  7/1972  Charle et al. .................... 128/200.14

OTHER PUBLICATIONS

"Bronchial Effects of Aerolized Δ9-tetrahydrocannabinol in Healthy Asthmatic Subjects" Tashkin et al., American Review of Respiratory Disease, vol. 115, 1977.

Primary Examiner—V. Millin
Attorney, Agent, or Firm—Keith D. Beecher

[57] ABSTRACT

This invention provides a process for the inclusion of a solid particulate component into self-propelled aerosol formulations of inhalable nicotine.

1 Claim, 1 Drawing Figure

PROCESS FOR THE INCLUSION OF A SOLID PARTICULATE COMPONENT INTO AEROSOL FORMULATIONS OF INHALABLE NICOTINE

RELATED APPLICATIONS

Ser. No. 830,052, filed Sept. 2, 1977 in the name of Allen W. Jacobs now abandoned.

BACKGROUND OF THE INVENTION

Numerous attempts have been made and means proposed to eliminate or lessen many of the negative and dangerous effects from the consumption of nicotine and cannabis. Herein, nicotine is used to refer to itself, the major active substance in tobacco. Also it is intended to refer to all relevant tobacco-like products, nicotine salts, derivatives, precursors, and those substances known to have nicotine-like effects, such as lobeline, the tetramethylamonium family of salts, etc. Cannabis is intended to refer to all of the relevant known substances found in the Cannabis family of plants. Also, it is intended to include all relevant cannabis-like products, natural and synthetic cannabis isomers, and other derivatives, precursors, metabolites, etc., or related substances having cannabis like effects.

While many means of consumption are known, not all are practical. The act of smoking, thus far, has proven to be one of the most direct, simple, and convenient means of intake of these substances.

Smoking involves the direct combustion of tobacco or cannabis and subsequent inhalation of the resulting smoke. This smoke may be inhaled directly in its raw form, immediately, or after it has been processed, filtered, or stored for use at a later time. As the active agents of tobacco and cannabis are relatively potent substances, only small amounts carried directly into the alveoli of the lungs and subsequently diffused into the bloodstream are needed to provide effect. As a result of this nearly direct access to the bloodstream, the relatively compact, simple to use, mild tasting, and yet potent means of consumption provided generally by smoking, and more specifically by the cigarette, in one form or another, has become the most popular means of tobacco and cannabis consumption, worldwide.

This does not include, however, the recent exception of cannabis preparations used medically in the United States. The most common of these is a capsule taken orally.

Smoking is not without its inherent problems, virtually all of which are well known and documented. For these reasons, smoking is not an approved medical means for the administration of any substance.

One of the major problems of smoking is the process of combustion itself required to produce the smoke for consumption. Kummel, in 1957, proposed the storage of compressed smoke for later use, thereby eliminating the need for combustion at the time of consumption. This means of consumption is not without disadvantage, however, in that the "tar", unwanted gases, and other byproducts of combustion are included in the smoke inhaled by the user.

The filtration and/or processing of smoke by all but the most esoteric means is both complex and incomplete. Known practical means such as cigarette filters, though widespread in use, have not been perfected. Additionally, they are almost totally ineffective against combustion gases without removing all other components simultaneously. "Perfect" filtration of stored or raw smoke, by measurement, would be exceedingly difficult to effect, and highly inefficient in the use of raw product, if attempted in practice. Combustion gases, which are present in stored smoke as they are in raw smoke, are likewise difficult to remove from all other components in the smoke without dramatically effecting the character and composition of the remaining components.

Proposals and experimentation, to extract or synthesize the active and desirable components and other additives judged necessary in the practice of the art to prepare any of various smokeless inhalable aerosol formulations, have been proposed and examined by Collier, Herxheimer, Olsen, Vachon, Tashkin, Jacobs (application Ser. No. 830,052, now abandoned), and others. Collier first proposed this means for the substitution of smoking tobacco in 1964. Herxheimer, in 1967, experimented with inhalable nicotine using a "Medihaler" aerosol dispenser and found it to be as physiologically effective as a means of providing inhalable nicotine to a user, as is a cigarette, without the necessity of producing or inhaling smoke. Likewise, in 1977, Gori proposed the effectiveness of a smokeless nicotine aerosol through use of a Babbington Inhaler.

Olsen developed a self propelled inhalable aerosol of delta-9-tetrahydrocannabinol and evaluated it on a preliminary basis in 1975. The effectiveness of delta-9-tetrahydrocannabinol in an inhalable aerosol, as a bronchodilator, was demonstrated through use of a cascade nebulizer by Vachon in 1976. Its bronchodilator effects were earlier verified by both Tashkin and Vachon, in smoke, in 1973.

Many methods of aerosol production described in the literature (i.e., ultrasonic nebulization, cascade nebulization, etc.) are effective in providing the user with a smokeless aerosol of sufficiently fine particle size to negotiate entry into the alveoli of the lungs in the same manner as smoke. They are, however, impractical for other than experimental use, due to their expense, size, lack of portability, and complexity.

The effectiveness of the various self propelled aerosol formulations examined, containing only liquid components, has varied. Depending upon the active agent under investigation, formulation involved, and intended purpose, estimated performance has ranged from marginal to good.

The inclusion of a finely divided, biologically inhert and/or compatable solid particulate fraction into a self propelled aerosol formulation is known to the art of self propelled inhalable aerosol medications. These include inhalable bronchodialators and steriods for asthma, and other formulations. It has proven to be both a feasable and practical process for the production of self propelled aerosols of sufficiently fine particle size to reach the alveoli of the lungs and, thereby, to deliver the active agent contained within or upon them to both the entire respiratory tree and, subsequently, the bloodstream.

DESCRIPTION OF THE INVENTION

As noted cursorily in application Ser. No. 830,052 (now abandoned), the essence of this invention is the process of including a smokeless solid particulate fraction into an inhalable nicotine or cannabis formulation for the purpose of providing a self propelled aerosol of sufficiently small particle size to carry nicotine or cannabis to the respiratory tree and bloodstream. These agents may thereby be delivered by the same route as if by the inhalation of smoke. The use of smoke for this purpose is thus obviated.

According to Sciarra and Stoller, particles in the diameter range of approximately one half to five microns, with the majority being in the one micron size are optimally capable of respiratory deposition in man. Particle size may vary, in the practice of the art, according to the given formulation and means of delivery of any particular embodiment.

Smoke particles by comparison, ranging to diameters as small as 0.01 micron, according to Sanders, are not only inhaled, but subsequently exhaled without alveolar deposition because they remain in suspension while in the alveoli of the lungs. This exhaled fraction is, thus, lost to the user and released as "sidestream" smoke, into the user's immediate environment.

In any of various preferred embodiments, the solid particulate fraction shall contain the active agent, either adsorbed to its surface, absorbed throughout, microencapsulated within each particle, or be composed, in part or in whole, of a chemical derivative of either active agent family. These forms may be used singly or in combination, in a given embodiment. In all embodiments, the active agent shall be released subsequent to contact of the aerosol with the respiratory tissues, either immediately, or over a period of time.

With this process, undesirable components found in smoke need not be included in an aerosol formulation embodying this invention, nor need an undesirable substance ever be removed from the aerosol by filtration, or other means. By the inclusion of a solid particulate fraction, aerosol particle size may be made to more closely match the optimum size range of non-exhaled smoke particles, than by any other self propelled aerosol means thus far proposed.

As noted in application Ser. No. 830,052 (now abandoned), other additives and adjuncts such as flavorings, buffers, surfactants, etc., may be included in both the solid particulate and also the nonparticulate fractions of the formulation.

Embodiments prepared in accordance with this invention may be inhaled by the user directly from aerosol containers as illustrated in FIG. 1 or by other means.

Although the scope of this invention is not limited to the embodiments herein taught, examples of solid particulate fractions include, but are not limited to: talc, dextrose or other carbohydrates, various physiological salt systems such as a lactated Ringer's system, non-physiological but biocompatable ionizing and/or non-ionizing systems, various insoluble systems such as finely powdered aluminum or magnesium that may be cleared and/or dissolved over time, or other solids that may be found feasable in the practice of the art. Any of various nicotine salt systems carrying nicotine, for example, would also be included in the spirit of the invention. Likewise, combinations of the above examples and other formulations are within its scope.

What is claimed is:

1. A process for the addition of a solid particulate component into a smokeless inhalable aerosol, which comprises the steps of providing a smokeless inhalable aerosol having nicotine as an active component; and introducing a solid particulate component into said smokeless inhalable aerosol with said nicotine being carried by the particulate component, in which the particle size of said solid particulate component is sufficiently fine to negotiate entry and deposition into the alveoli of the lungs and closely matches the optimum size range of non-exhaled smoke particles.

* * * * *